(12) United States Patent
Heath

(10) Patent No.: US 8,449,440 B2
(45) Date of Patent: May 28, 2013

(54) APPARATUS FOR AUTOMATIC TRACKING AND IDENTIFICATION OF DEVICE COMPONENTS

(75) Inventor: Christopher Heath, Benenden (GB)

(73) Assignee: Varian Medical Systems UK Limited, West Sussex (GB)

(*) Notice: Subject to any disclaimer, the term of this patent is extended or adjusted under 35 U.S.C. 154(b) by 119 days.

(21) Appl. No.: 12/761,321

(22) Filed: Apr. 15, 2010

(65) Prior Publication Data

US 2010/0197991 A1 Aug. 5, 2010

Related U.S. Application Data

(62) Division of application No. 11/017,980, filed on Dec. 20, 2004, now Pat. No. 7,722,521.

(51) Int. Cl.
*A61M 36/00* (2006.01)

(52) U.S. Cl.
USPC .................................. 600/7; 600/3

(58) Field of Classification Search
USPC ........... 600/1–8, 103, 117, 118; 128/897–899
See application file for complete search history.

(56) References Cited

U.S. PATENT DOCUMENTS

| | | |
|---|---|---|
| 4,150,298 A | 4/1979 | Brault et al. |
| 4,969,863 A | 11/1990 | van't Hooft et al. |
| 5,030,194 A | 7/1991 | Van't Hooft et al. |
| 5,139,473 A | 8/1992 | Bradshaw et al. |
| 5,800,333 A | 9/1998 | Liprie |
| 6,366,206 B1 | 4/2002 | Ishikawa et al. |
| 6,575,891 B1 | 6/2003 | Castelo et al. |
| 6,847,856 B1 | 1/2005 | Bohannon |
| 6,968,994 B1 * | 11/2005 | Ashwood Smith ........... 235/375 |
| 7,399,269 B2 | 7/2008 | Kindlein et al. |
| 2002/0096180 A1 * | 7/2002 | Teller ............................ 128/897 |

FOREIGN PATENT DOCUMENTS

| | | |
|---|---|---|
| EP | 0791374 | 8/1997 |
| EP | 1445002 | 8/2004 |
| WO | WO-0074778 | 12/2000 |

OTHER PUBLICATIONS

"tube." Roget's 21st Century Thesaurus, Third Edition. Philip Lief Group 2009. Aug. 25, 2011. <Thesaurus.com http://thesaurus.com/browse/tube>.*
"network." Collins English Dictionary 2000. Aug. 25, 2011. <http://www.credoreference.com/entry/hcengdict/network>.*
PCT Search Report mailed Feb. 23, 2006; PCT/GB2005/004741.

* cited by examiner

*Primary Examiner* — Charles A Marmor, II
*Assistant Examiner* — Carrie R Dorna
(74) *Attorney, Agent, or Firm* — Blakely, Sokoloff, Taylor & Zafman LLP

(57) ABSTRACT

Embodiments of an apparatus and method to track and identify radioactive sources are described. In one embodiment, a device includes first housing for a radioactive source having a first electronic tag, a second housing for the radioactive source having a second electronic tag, and a guide tube that couples the first housing with the second housing. The guide tube includes a third electronic tag. The first, second, and third electronic tags communicate with each other to confirm automatically a delivery path for the radioactive source. In one embodiment, the electronic tags may be a radio frequency identification device (RFID).

23 Claims, 10 Drawing Sheets

APPARATUS FOR AUTOMATIC TRACKING AND IDENTIFICATION OF DEVICE COMPONENTS

RELATED APPLICATION

This application is a divisional of co-pending U.S. patent application Ser. No. 11/017,980, filed Dec. 20, 2004, titled "METHOD AND APPARATUS FOR AUTOMATIC TRACKING AND IDENTIFICATION OF DEVICE COMPONENTS".

TECHNICAL FIELD

Embodiments of the present invention relate to the field of tracking and identifying device components, and more specifically, to the tracking and identifying of radioactive sources used with an afterloader.

BACKGROUND

Radiation is one method to treat cancer and other diseases of the body. Brachytherapy is a general term for the radiation treatment of cancer at close distances inside the body. During brachytherapy, an applicator enclosing a radioactive source or sources is positioned within a body region targeted for treatment. The radioactive sources are typically wires with an end portion that emits radiation, or alternatively capsule type structures of radioactive materials. As used herein, the term radioactive source encompasses wires, capsules or other structures of radioactive materials In one type of brachytherapy, radioactive sources are temporarily placed in target treatment regions in the patient. To prevent human handling of the radioactive material and harmful exposure to radiation, a machine called an "afterloader" or "remote afterloader" may be used to load and unload the radioactive material into and from guide tubes that extend toward the applicator positioned within a patient.

Remote afterloaders allow for the accurate advancement and retraction of radioactive sources over a specified distance for a specified time period. A remote afterloader generally includes multiple channels, may hold more than one radioactive source, and uses controllers and drive mechanisms to advance and retract the radioactive source(s) through multiple ports attached to a rotating wheel that allows multiple guide tubes (previously placed into the patient) to be hooked up to the afterloader at the same time. The remote afterloader usually sends out a simulation member to check the patency of the guide tube without subjecting the patient to undue radiation exposure, and then sends out the radioactive source. After the treatment is performed through a first guide tube, the afterloader retracts the source into the shielding safe inside the afterloader, a wheel turns and aligns the next slot containing a guide tube to the shielded safe exit port. The remote afterloader then repeats its function sending and retracting the simulation member and radioactive member through this second tube. The procedure is repeated until the treatment prescription is carried out through all the specified transport tubes. FIG. 1 shows a prior art afterloader with multiple guide tubes attached.

One problem with current afterloader systems is that in order to verify that the correct applicator channel is correctly attached to the planned treatment port of the afterloader via a guide tube, the operator must visually inspect the attachment of the applicator to the guide tube, and the attachment of the guide tube to the afterloader port. If multiple guide tubes are used for treatment, each attachment must be checked by the operator. Because this involves a manual process, the possibility of human error exists, which may result in the wrong treatment being administered to the patient. Another problem is that even though the correct applicator is attached to a guide tube, the operator may not notice that the attachment is not secure, resulting in the unwanted exposure of the radioactive source to the patient or operator. Current devices include a mechanical gate (as illustrated in FIG. 2) to prevent the radioactive source from being ejected uncontrollably into the patient, but a patient may still receive an unwanted whole body dose of radiation if the gate blocks or traps the radioactive source during retraction.

In a related problem, in order to exchange an old or used radioactive source contained in the afterloader for a new radioactive source, an operator has to attach one end of a guide tube to an empty chamber in a source container chamber, and then connect the other end of the guide tube to the afterloader, as illustrated in FIG. 3. The old radioactive source then has to be downloaded into an empty chamber in the source container chamber. Following the download, the radioactive source is locked into the chamber and the transfer guide tube is detached from the now occupied chamber of the source container chamber, and then reattached to the chamber containing the new radioactive source. The new source is then uploaded into the afterloader. At this point the operator has to manually enter the radioactive source serial number and calibration data into the afterloader computer system. Again, because this is a manual process, the uploading and downloading of radioactive sources, as well as the input of radioactive source data, is prone to human error. Problems related to the secure attachment of the guide tube to the afterloader and source container chamber also exist, as described above with respect to the attachment of an applicator to the guide tube.

SUMMARY

Embodiments of an apparatus and method to track and identify radioactive sources are described. In one embodiment, the radioactive source may be delivered from a first housing to a second housing through a guide or transport tube, or conversely from second housing to first housing. In one embodiment, the first housing may be an afterloader, a system for containing one or more radioactive sources for remote deployment under automatic control. The second housing may be a radioactive source applicator, which is an end portion that is inserted into the treatment region of a patient (e.g., for exposure to radiation with the radioactive source). In an alternative embodiment, the second housing may be a radioactive source container for the uploading and/or downloading of one or more radioactive sources to and from the afterloader. Because of the dangers associated with handling radioactive materials, identifying and tracking the various device components used for the delivery of radioactive materials are important for the device operator, as well as ensuring that the proper therapeutic treatment is administered.

In one embodiment, identification and tracking of radioactive materials (e.g., a radioactive source) may be provided by one or more electronic identification tags disposed on components of the device. For example, a first electronic tag may be disposed on the first housing, a second electronic tag may be disposed on the second housing, and a third electronic tag may be disposed on guide tube. The electronic identification tags may communicate with each other wirelessly to provide data relating to the connection of each component, as well as other types of audit data. In one embodiment, the electronic identification tags may be radio frequency identification devices. The radioactive source may be transported by being attached to a cable, wire or similar structure, or transported by pneumatic, hydraulic or electromagnetic mechanisms. It will be understood that while a particular method of transport may be described in conjunction with a particular embodiment, other methods of transport, including the foregoing, may be used.

BRIEF DESCRIPTION OF THE DRAWINGS

The present invention is illustrated by way of example, and not limitation, in the figures of the accompanying drawings in which.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form.

Embodiments of a medical device having identification and tracking abilities for device components are described. In one embodiment, a delivery path for a radioactive source from a first housing to a second housing may be identified and tracked. For example, in one embodiment of the present invention, a device for the delivery of a therapeutic radioactive material may include an afterloader, a guide tube, and an applicator. Electronic identification tags may be disposed on each of the device components to provide information such as connection, tracking information, and other audit data which may be valuable when dealing with radioactive sources. In another embodiment of the present invention, a guide tube may be used to couple an afterloader with a radioactive source storage container. When a radioactive source is either uploaded or downloaded from the storage container, electronic tags disposed on the afterloader, guide tube, and storage container may communicate information such as radioactive source information, delivery path, and secure connection data to the afterloader. In one embodiment, the electronic tags may be radio frequency identification device (RFID) tags that may be disposed on the device components or embedded within the components to provide wireless communication of information. The use of RFID tags eliminates the possibility of human error in handling radioactive sources, as well as providing accurate, automatic tracking and identification of radioactive sources and delivery paths.

Figure 1:
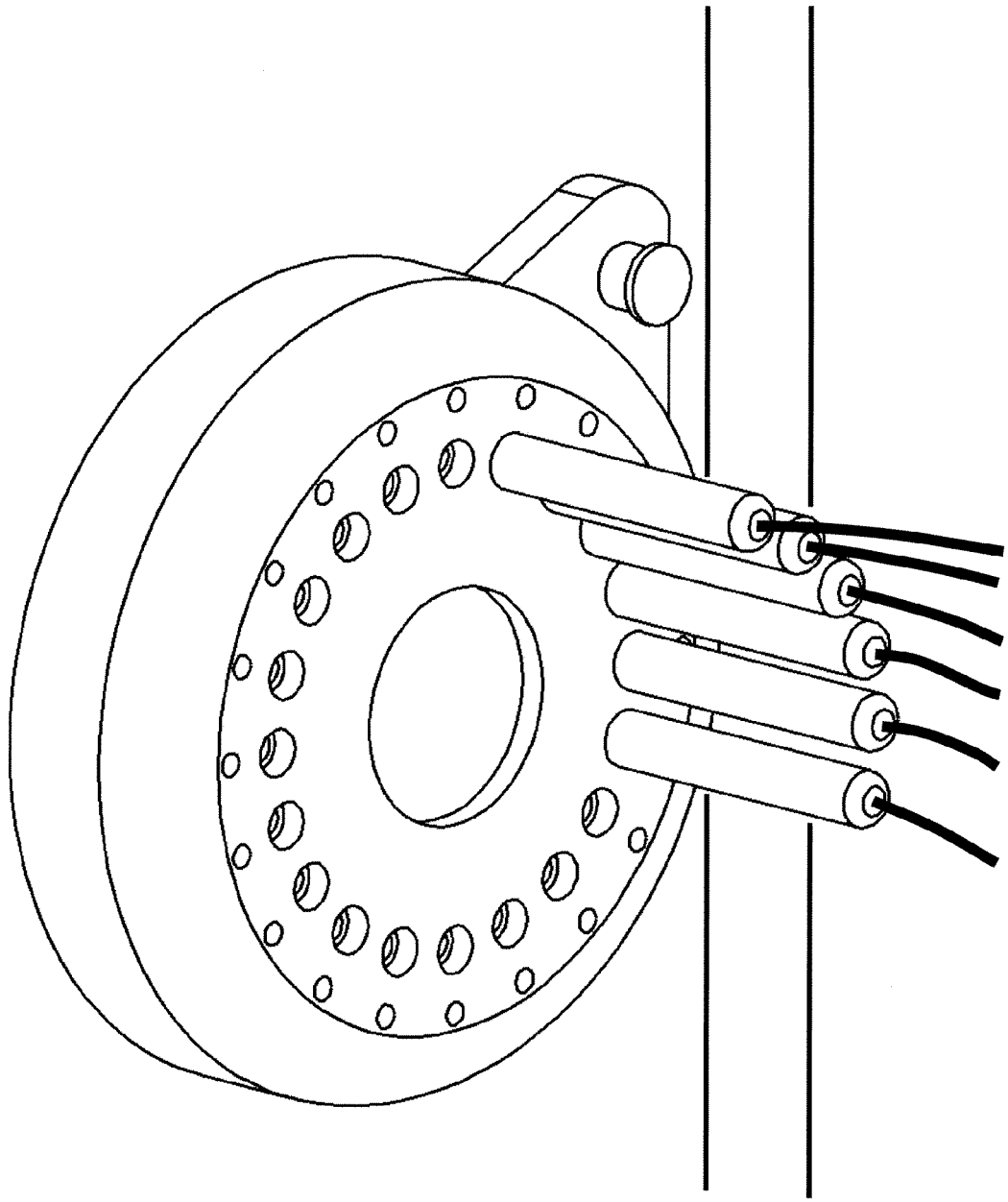
FIG. 1 illustrates a prior art afterloader.
Figure 2:
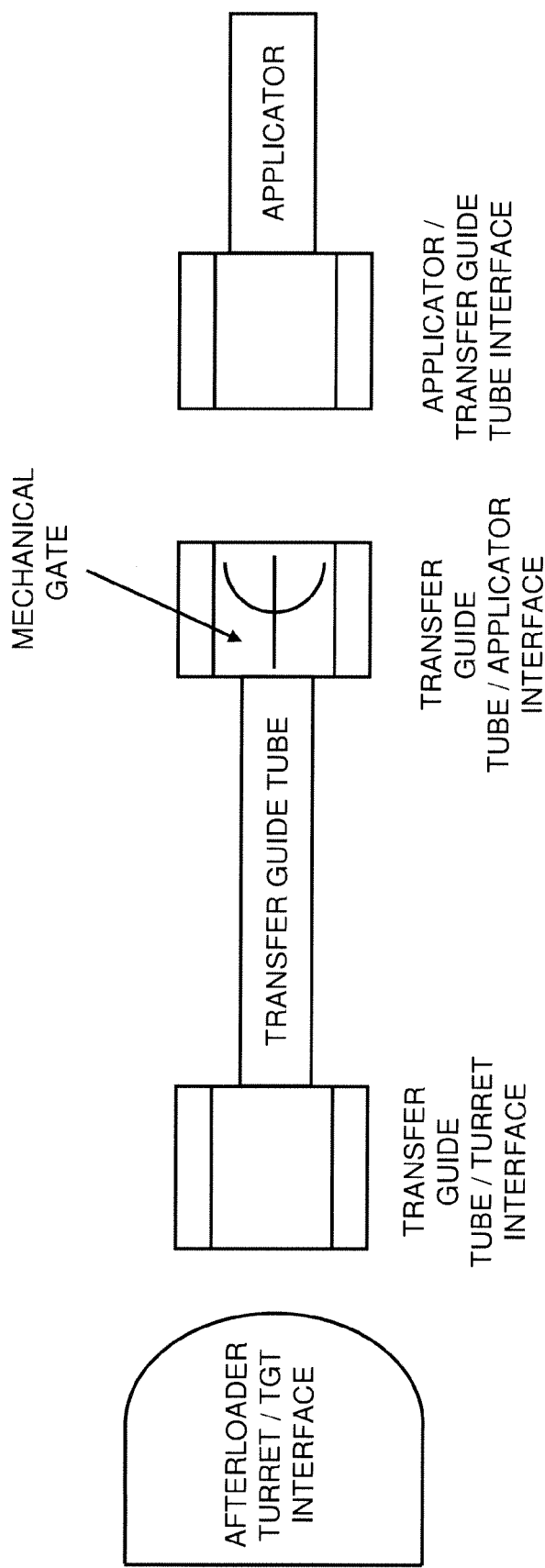
FIG. 2 illustrates another prior art afterloader coupled to an applicator.
Figure 3:
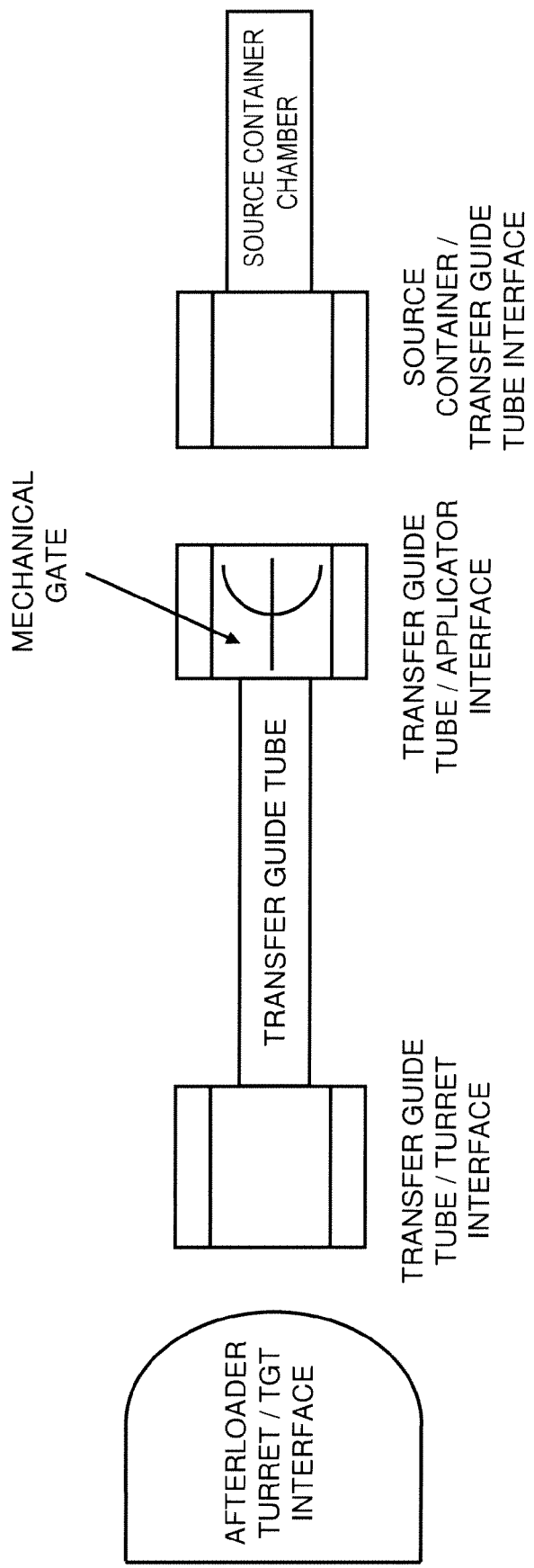
FIG. 3 illustrates a prior art afterloader coupled to a source storage container.
Figure 4:
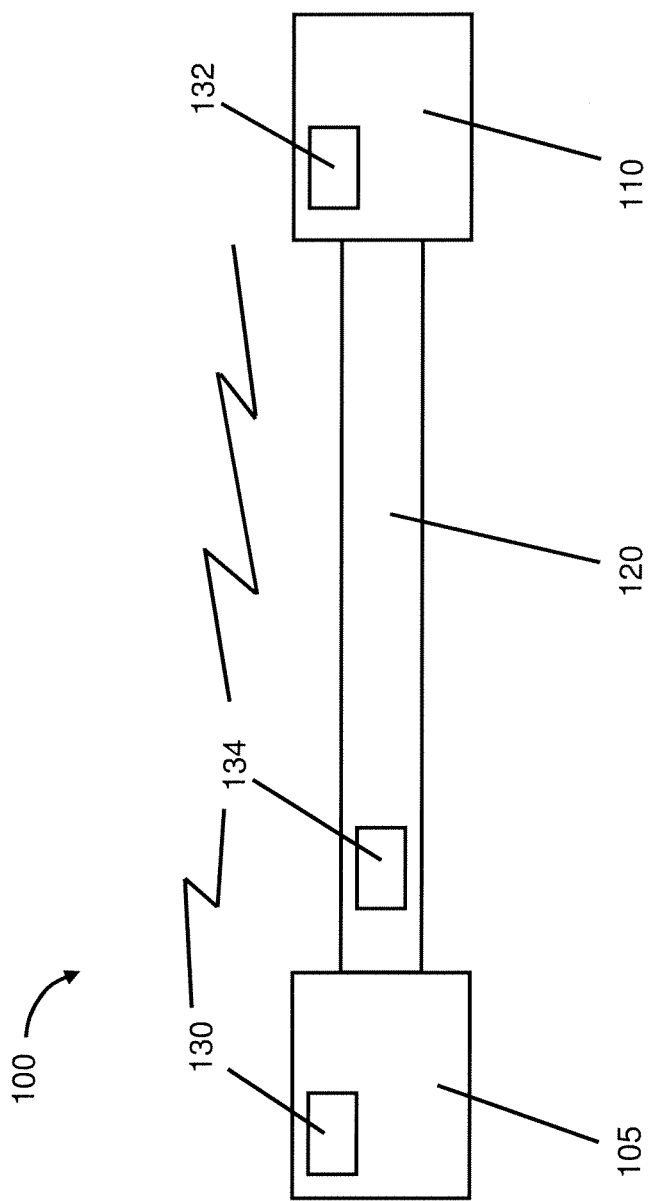
FIG. 4 illustrates one embodiment of medical device that may be used track and identify the delivery of a radioactive source from one point to another.

FIG. 4 illustrates a generic representation of one embodiment of a medical device 100 that may be used track and identify the delivery of a radioactive source (not shown) from one point to another. In one embodiment of the present invention, the radioactive source may be delivered from a first housing 105 to a second housing 110 through a guide or transport tube 120, or conversely from second housing 110 to first housing 105. In one embodiment, first housing 105 may be an afterloader, a system for containing one or more radioactive sources for remote deployment under automatic control. The second housing 110 may be a radioactive source applicator, which is an end portion that is inserted into the treatment region of a patient (e.g., for exposure to radiation with the radioactive source). In an alternative embodiment, second housing 110 may be a radioactive source container for the uploading and/or downloading of one or more radioactive sources to and from the afterloader. Because of the dangers associated with handling radioactive sources, identifying and tracking the various device components used for the delivery of radioactive sources are important for the device operator, as well as ensuring that the proper therapeutic treatment is administered.

In one embodiment, identification and tracking of (e.g., a radioactive source capsule or cable) may be provided by one or more electronic identification tags disposed on components of medical device 100. For example, a first electronic tag 130 may be disposed on first housing 105, a second electronic tag 132 may be disposed on second housing 110, and a third electronic tag 134 may be disposed on guide tube 120. The electronic identification tags may communicate with each other wirelessly to provide data relating to the connection of each component, as well as other types of audit data. The electronic identification tags provide the advantage of automating communication between device components, thereby eliminating the need for manual input of data relating to each device component and radioactive source.

Figure 5:
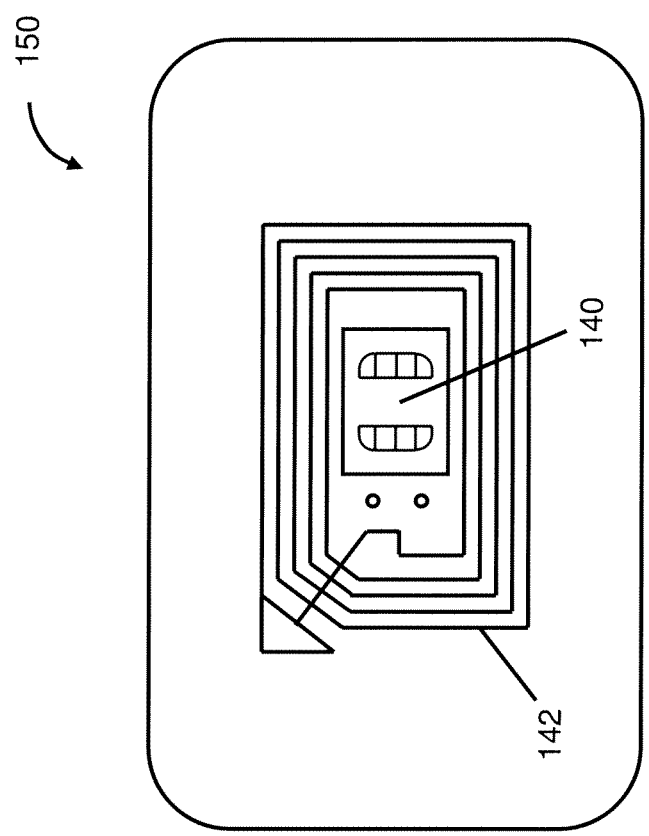
FIG. 5 illustrates one embodiment of a radio frequency identification device that may be used with the medical device of FIG. 4.

In one embodiment, the electronic identification tags (e.g., tags 130, 132, 134) may be a radio frequency identification device (RFID). FIG. 5 illustrates one embodiment of a RFID tag 150 that may be used as an electronic identification tag (e.g., tag 130) disposed on any one of the device components. In one embodiment, RFID tag 150 includes information for the identification and tracking of a particular component to which the tag is associated, and is also able to communicate information with other RFID tags disposed on other components (e.g., tags 132 and 134). RFID tag 150 may include a small IC microchip 140 coupled to an antenna 142 (alternatively, the microchip and antenna together may also be referred to as a RFID transponder or RFID tag). Antenna 142 enables microchip 140 to transmit identification information or other data to a RFID reader (not shown) or another RFID tag. The reader converts the radio waves reflected back from the RFID tag into digital information that can then be passed on to application systems (e.g., an afterloader controller) for use in devising a therapeutic treatment procedure. It may be appreciated that the RFID tags do not necessarily have be disposed on the particular areas of device 100 as illustrated, but may be disposed on any portion of a particular device component, including being embedded within a particular component so that the tags are not exposed.

In one embodiment, the RFID tags may be part of a larger RFID system that includes the RFID tags and an interrogator or reader coupled to an antenna. The reader sends out electromagnetic waves and each RFID tag antenna is tuned to receive these waves. In one embodiment, the RFID tags may be passive devices which draw power from a field created by the reader and uses it to power the microchip's circuits. The chip then modulates the waves that the tag sends back to the reader and the reader converts the new waves into digital data. As such, power to a microchip for a RFID tag may be supplied when in the vicinity of a reader. In an alternative embodiment, the RFID tags may be active devices. Active RFID tags have a battery, which is used to run the microchip's circuitry and to broadcast a signal to a reader or another RFID tag. In yet another embodiment, RFID tags may be semi-passive RFID devices, which use a battery to run the chip's circuitry, but communicate by drawing power from the reader. Microchips in RFID tags can be read-write or read-only. With read-write chips, information may be added, deleted, edited, or written over existing information when the tag is within range of a reader, interrogator, or another RFID tag.

Figure 6:
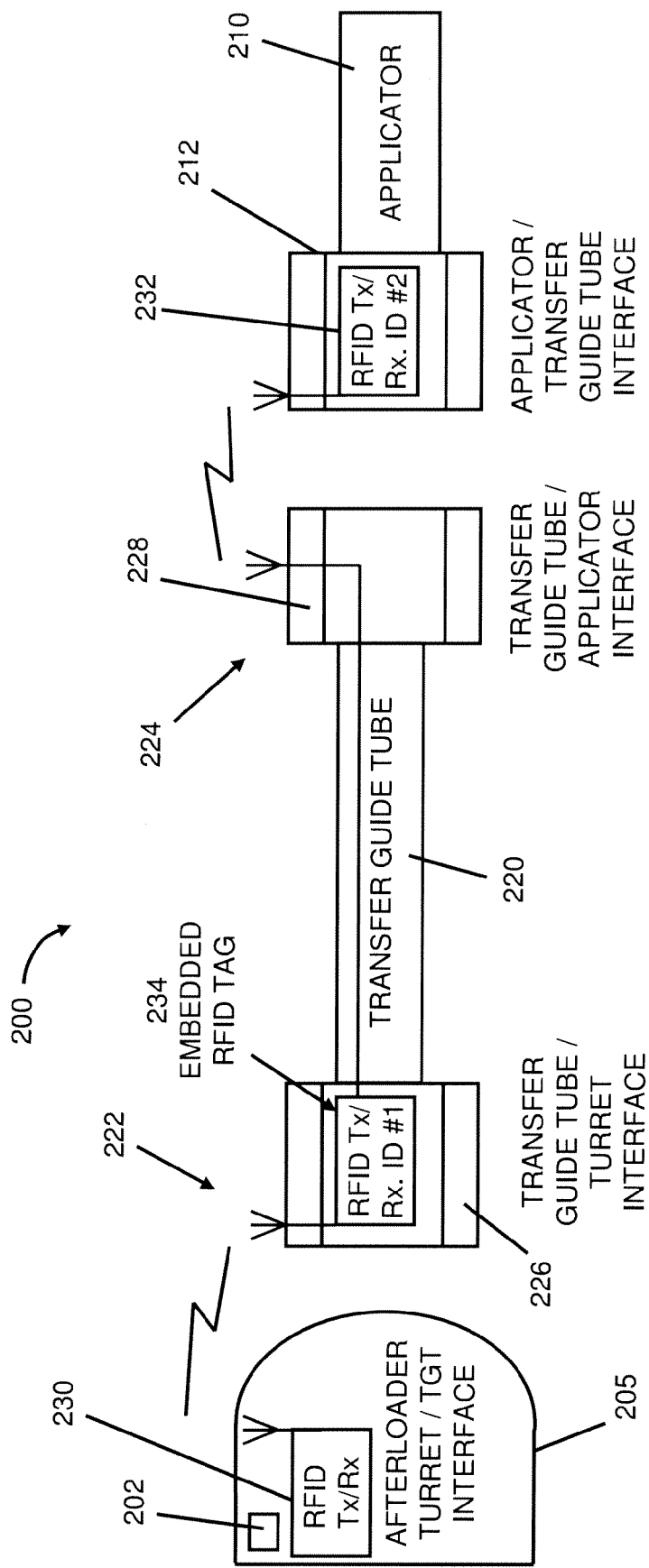
FIG. 6 illustrates one embodiment of a medical device that may be used to deliver a radioactive source from an afterloader to an applicator through a guide tube.

FIG. 6 illustrates one embodiment of a medical device 200 that may be used to deliver a radioactive source from an afterloader to an applicator through a guide tube, while providing tracking and identification capabilities through the use of electronic tags. Device 200 represents an afterloader system that includes afterloader 205 coupled to applicator 210 with guide tube 220. For clarity of explanation in describing each device component, afterloader 205 and applicator 210 are shown separated from guide tube 220. In one example of using device 200 for the delivery of a radioactive source for therapeutic purposes, a treatment plan is devised that involves determining a delivery path of the radioactive source (e.g., a radioactive source capsule) from Afterloader 205 through guide tube 220, and with the source capsule application through the applicator 210.

The determination of a delivery path may be necessary when using an afterloader 205 that includes multiple ports for the coupling of multiple guide tubes (e.g., guide tube 220) simultaneously. For example, afterloader 205 may include multiple radioactive source wires disposed in individual channels that extend toward a turret of ports (not shown). The radioactive source wires may be of different radiation levels to provide a variety of dosage levels for therapeutic delivery. The turret rotates to align a particular channel for delivery of the desired radioactive source capsule. Accordingly, a particular treatment plan may include a delivery of a first radioactive source capsule through a first channel, a first guide tube, and a first applicator, followed by a second delivery of a second radioactive source capsule through a second channel, a second guide tube, and a second applicator. In one embodiment, afterloader 205 may be one of several afterloaders known in the art, including but not limited to, high dose rate afterloaders (HDR), low dose rate afterloaders (LDR), pulse dose rate afterloaders (PDR), and low energy rate afterloaders (LER). In another embodiment, applicator 210 may include multiple channels for delivery different radioactive sources, so that a new applicator does not need to be coupled when delivering a new radioactive source from afterloader 205. One type of afterloader is the VariSource High Dose Remote Afterloader, manufactured by Varian Medical Systems of Palo Alto, Calif.

In one embodiment for coupling guide tube 220 to afterloader 205 and applicator 210, a first end 222 of guide tube 220 includes a first interface 226 for coupling to afterloader 205. A second end 224 of guide tube 220 includes a second interface 228 for coupling to a third interface 212 of applicator 210. Any type of interfaces known in the art may be used to secure the coupling of guide tube 220 to afterloader 205 and applicator 210. A first RFID tag 230 is disposed on afterloader 205, a second RFID tag 232 is disposed on applicator 210, and a third RFID tag 234 is disposed on guide tube 220. In one embodiment, each RFID tag may be attached to an outer surface of each component of device 200 (e.g., applicator 210). In an alternative embodiment, each RFID tag may be embedded within a wall of the component. Each RFID tag may include various types of information for the identification and/or tracking of a particular device component. For example, with respect to RFID tag 232 associated with applicator 210, information such as a unique identification tag number, date of manufacture, and lot number may be stored. RFID tag 232 may also identify applicator 210 as either a single use applicator, or a multiple use applicator for the delivery of a radioactive source to a treatment region of a patient.

In one embodiment, a controller 202 disposed on afterloader 205 coordinates the communication between the various RFID tags disposed throughout device 200. For example, information from RFID tag 232 disposed on applicator 210 is relayed to RFID tag 230 disposed on afterloader 205 through RFID tag 234. Information relayed from RFID tag 232 to RFID tag 230 may be used to ensure that the delivery path for the radioactive source is consistent with the planned treatment for a patient prior to starting the actual radiation exposure. For example, afterloader 205 may confirm whether applicator 210 is a single use applicator or a multiple use applicator. If applicator 210 is a single use applicator, afterloader 205 may confirm that applicator 210 has not been previously used. If applicator 210 is a multiple use applicator, information related to the age of applicator 210, the number of use cycles may be relayed to RFID 230.

Another advantage provided by the use of the RFID tags is providing a confirmation as to which particular applicator and/or guide tube is coupled to afterloader 205, and in a related manner, confirm that the guide tube and applicator are properly attached to each other and to afterloader 205 as well. This communication is particularly useful if applicator 205 includes multiple channels or if multiple applicators are employed, because any error associated with an incorrect connection to an applicator or guide tube is eliminated. Consequently, the delivery of a radioactive source is prevented should an improper coupling exist. These and other related information are provided through the communication of the RFID tags allowing an operator of afterloader 205 to make a determination as to whether to commence with a particular therapeutic treatment. Any need for manually inspecting the applicators and guide tubes coupling is removed, avoiding the need to inspect the coupling manually and the introduction of human error. In an alternative embodiment, RFID tag 232 disposed on applicator 210 may communicate directly with RFID tag 320 without a relay through RFID tag 234 disposed on guide tube 220.

As discussed above, the RFID tags (e.g., RFID tag 232 disposed on applicator 210) may either be read-only or read-write. For a read-write RFID tag, additional data may be stored (i.e., "re-tagged") in memory related to use-history, number of cycles, and sterilization history. For example, for a reusable or a multi-use applicator, sterilization dates may be stored on the RFID tag after the applicator undergoes a sterilization procedure so that an operator may compare that date to the last time the applicator was used with an afterloader. Inventory data may also be stored on the RFID tag, for example, in tracking the history of an applicator from production to disposal. Hospitals may be able to use this tracking data in the event that an applicator manufacturer issues a recall, applicators that are the subject to the recall may be identified easily. Although device 200 has been described with respect to the storage and communication data from applicator 210, it may be appreciated that similar types of information may be stored on RFID tag 320 and 322 for transmission with other RFID tags disposed device 200.

Figure 7:
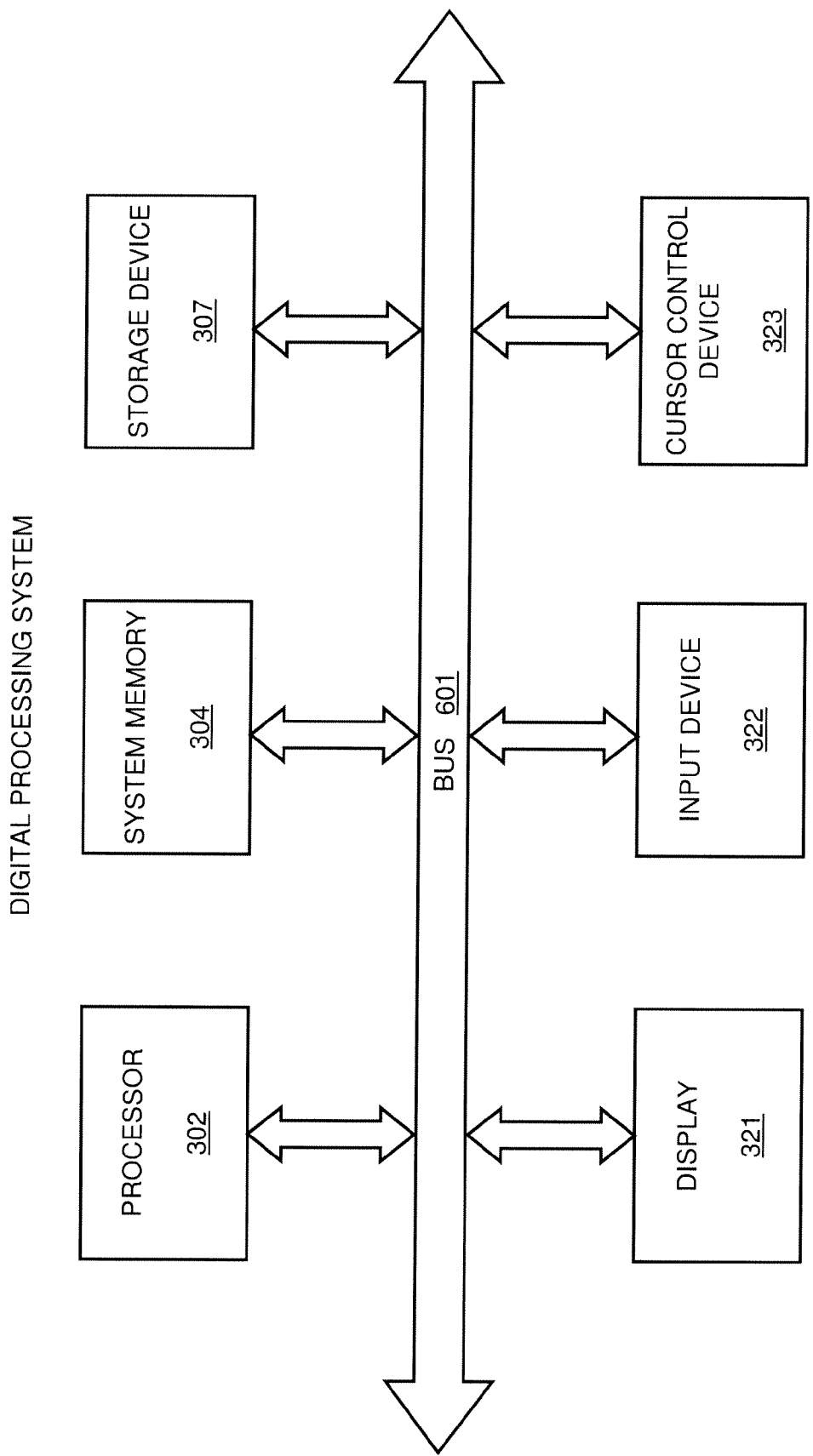
FIG. 7 illustrates an exemplary machine in the form of a computer system that is integrated within the afterloader of FIG. 6 for controlling the communication between the multiple RFID tags.

FIG. 7 illustrates a controller (e.g., controller 205) in the form of a computer system 300 that may be integrated within afterloader 205 for controlling the communication between the multiple RFID tags disposed on device 200. Computer system 300 includes a bus or other communication means 301 for communicating information, and a processing means such as processor 302 coupled with bus 301 for processing information. Computer system 300 further includes a random access memory (RAM) or other dynamic storage device 304 (referred to as main memory), coupled to bus 301 for storing information and instructions to be executed by processor 302. Main memory 304 also may be used for storing temporary variables or other intermediate information during execution of instructions by processor 302. Computer system 300 also includes a read only memory (ROM) and/or other static storage device 306 coupled to bus 301 for storing static information and instructions for processor 302.

A data storage device 307 such as a magnetic disk or optical disc and its corresponding drive may also be coupled to computer system 300 for storing information and instructions. The data storage device 307 may be used to store instructions for performing the steps discussed herein. Processor 302 may be configured to execute the instructions for performing the steps discussed herein. Computer system 300 can also be coupled via bus 301 to a display device 321, such as a cathode ray tube (CRT) or Liquid Crystal Display (LCD), for displaying information to an end user. For example, graphical and/or textual depictions/indications of design errors, and other data types and information may be presented to the end user on the display device 321. Typically, an alphanumeric input device 322, including alphanumeric and other keys, may be coupled to bus 301 for communicating information and/or command selections to processor 302. Another type of user input device is cursor control 323, such as a mouse, a trackball, or cursor direction keys for communicating direction information and command selections to processor 302 and for controlling cursor movement on display 321.

Figure 8:
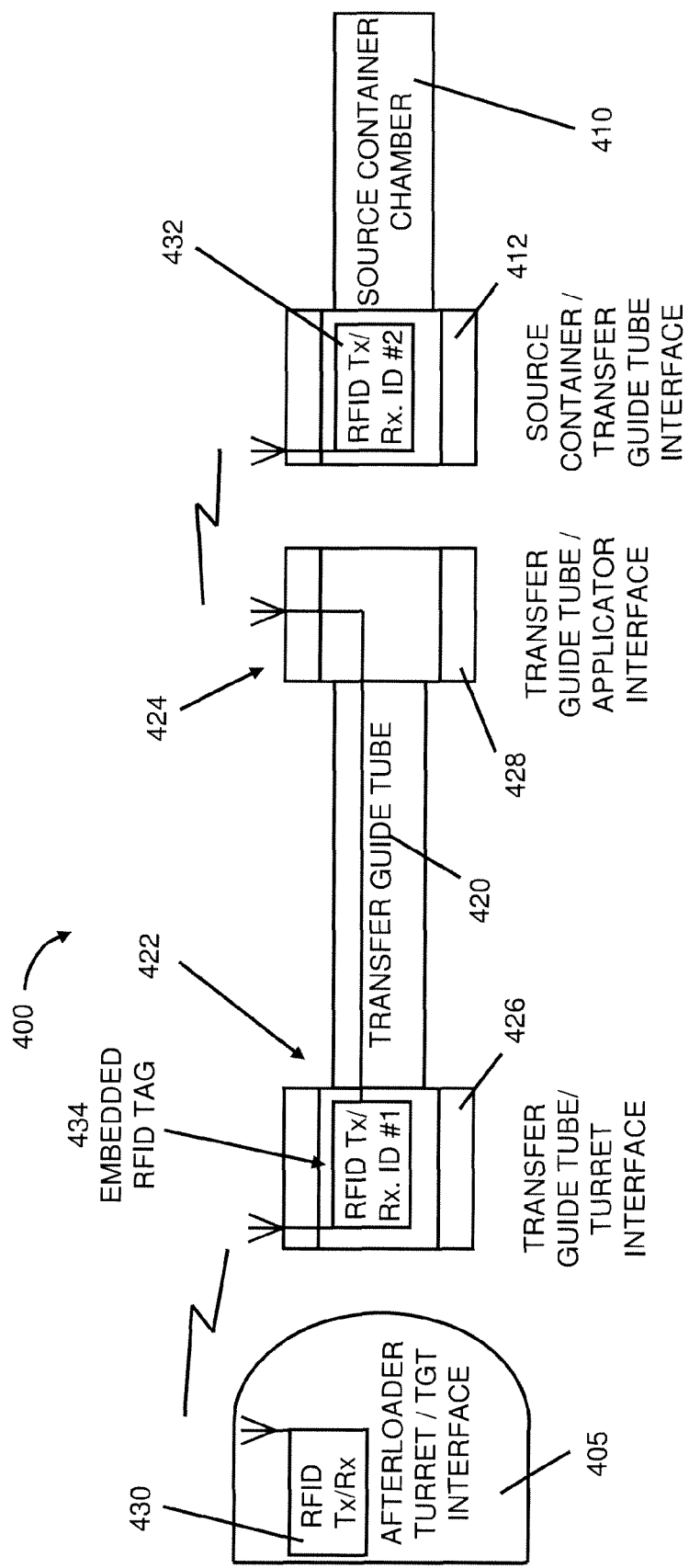
FIG. 8 illustrates another embodiment of a configuration for an afterloader device to deliver a radioactive source from one housing area to another housing area.

FIG. 8 illustrates another embodiment of a configuration for afterloader device 400 to deliver a radioactive source from one housing area to another housing area. Remote afterloaders will, from time to time, require the uploading or downloading of radioactive source capsules from a storage container in order to replace used source capsules. To prevent exposure to an operator, afterloader 405 is coupled to source container chamber 410 with guide tube 420. Similar to the configuration described above with respect to device 200, a first end 422 of guide tube 420 includes a first interface 426 for coupling to afterloader 405. A second end 424 of guide tube 420 includes a second interface 428 for coupling to a third interface 412 of source container chamber 410. Any type of interfaces known in the art may be used to secure the coupling of guide tube 420 to afterloader 405 and source container chamber 410. In one embodiment, afterloader 405 may be one of several afterloaders known in the art, including but not limited to, HDR, LDR, PDR, and LER.

A first RFID tag 430 is disposed on afterloader 405, a second RFID tag 432 is disposed on source container chamber 410, and a third RFID tag 434 is disposed on guide tube 420. In one embodiment, each RFID tag may be attached to an outer surface of each component of device 400 (e.g., source container chamber 410). In an alternative embodiment, each RFID tag may be embedded within a wall of the component. Each RFID tag may include various types of information for the identification and/or tracking of a particular device component. For example, with respect to RFID tag 432 associated with source container chamber 410, information such as a unique identification tag number associated with a particular radioactive source capsule, radioactive source type, and source activity may be stored. Other tracking and identification advantageous are described in greater detail below.

When a new radioactive source capsule is uploaded from source container chamber 410 to afterloader 405, a signal or communication is sent from RFID tag 432 disposed on source container chamber 410 to RFID tag 430 disposed on afterloader 405. In one embodiment, the communication may be relayed through RFID tag 434 disposed on guide tube 420. The signal indicates to afterloader 405 that guide tube 420 has made a secure connection to source container chamber 410, as well as a secure connection of guide tube 420 to afterloader 405. In one embodiment, this indication may be determined by the presence or absence of a signal from RFID 432. The signal from RFID 432 may also include information such as, for example, serial number (e.g., of the new source capsule to be uploaded into afterloader 405), calibration data, date of manufacture, and lot number. It may be appreciated that other types of data may be communicated to afterloader 405.

Figure 9:
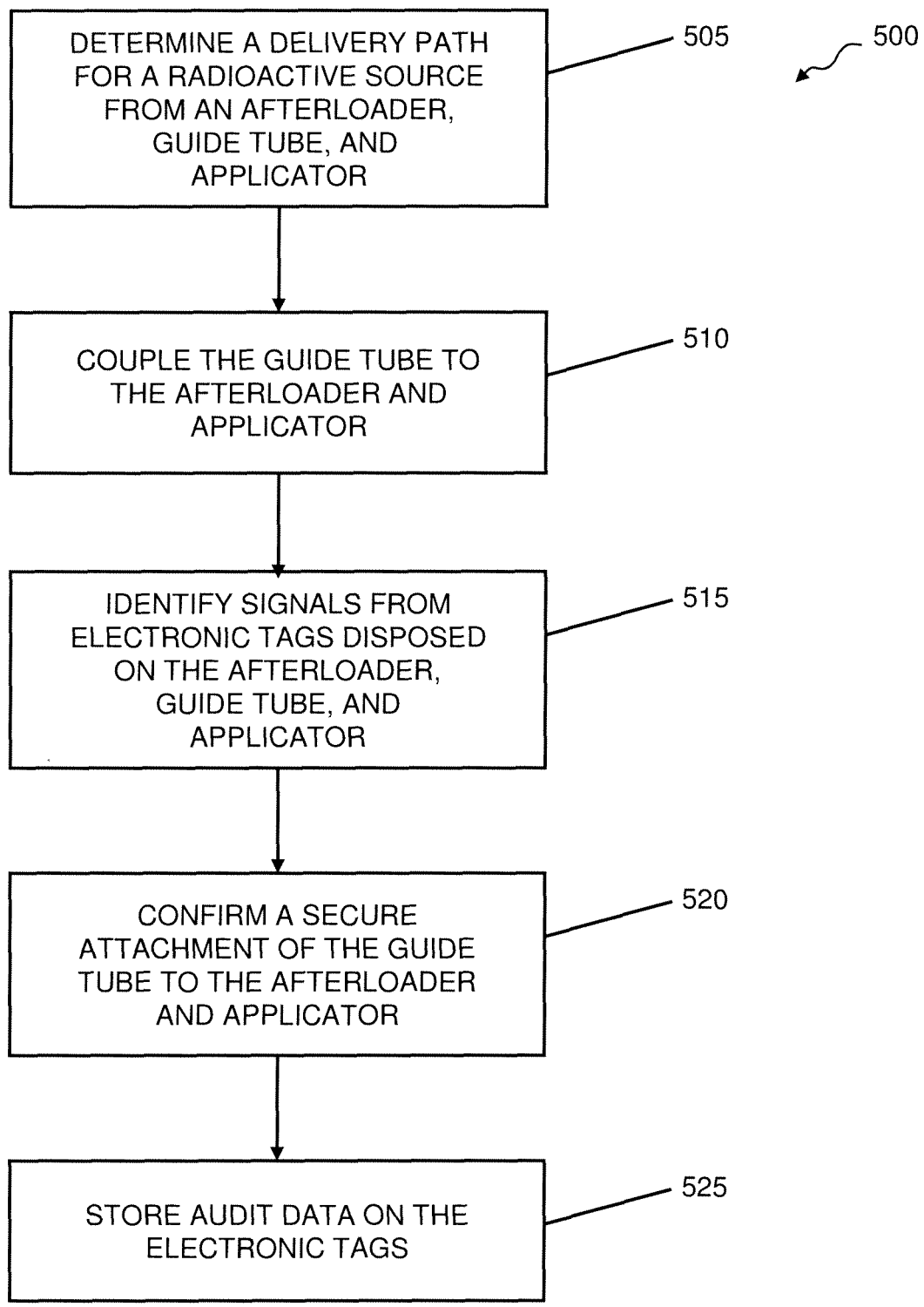
FIG. 9 illustrates a block diagram of one method to track and identify radioactive sources used with an afterloader.

FIG. 9 illustrates a block diagram 500 of one method to track and identify radioactive sources used with an afterloader automatically. An afterloader system may be used to delivery a radioactive source to a target region within a patient. A treatment plan is devised to deliver a particular radioactive source (e.g., a source capsule) from an afterloader to the patient. As such, a delivery path is determined that includes a channel from the afterloader (e.g., afterloader 205), guide tube (e.g., guide tube 220), and applicator (e.g., applicator 210), block 505. In one embodiment, the afterloader may include multiple radioactive sources disposed within individual channels that lead to ports for coupling to guide tubes, as well as multiple guide tubes coupled to the ports. A first end of a guide tube is coupled to the afterloader and a second end of the guide tube is coupled to the applicator, block 510. Alternatively, the afterloader may include multiple ports (e.g., up to 50 ports) with a guide tube coupled to each port. In one example of a prescribed treatment, a determination may be made to deliver a radioactive source through port #2 of the afterloader, through guide tube #2, and through channel #2 of a multi-channel applicator.

In order to send the radioactive source to the correct applicator channel to deliver the prescribed treatment, the correct applicator must be coupled to the correct guide tube, which must also be coupled to the correct port of the afterloader. A controller disposed on the afterloader identifies signals from electronic identification tags disposed on the afterloader, each guide tube, and each applicator to determine the correct path to send the radioactive source in order to deliver the prescribed treatment, block 515. For example, if the controller recognizes that guide tube #5 is coupled to port #2 instead of port #5, the controller may indicate to the operator that an incorrect coupling exists (that may result in the administration of an improper radioactive source). In one embodiment, once the afterloader controller has determined that guide tube #5 is coupled to port #2 instead of port #5, it can automatically adjust its prescribed treatment plan to take into account the misconnections, and instead send the correct treatment prescription for the applicator connected to guide tube 5 to port 2. In one embodiment, the electronic identification tags may be RFID tags (e.g., tags 230, 232). In addition to verifying that the prescribed delivery exists, the electronic tags may also confirm that the guide tube is securely attached to the afterloader and applicator (e.g., through the interfaces 226, 228 of guide tube 220), block 520. In one embodiment, the signal from the RFID tag disposed on the applicator (e.g., RFID tag 232) may be relayed through the RFID tag disposed on the guide tube (e.g., RFID tag 234) in order to reach the RFID tag disposed on the afterloader (e.g., RFID tag 230). Data may also be written and stored on the electronic tags to provide audit information for the device component, block 525. This may include, for example, applicator identification number, manufacture date, usage cycle, sterilization periods, and other types of device tracking and identification data.

Figure 10:
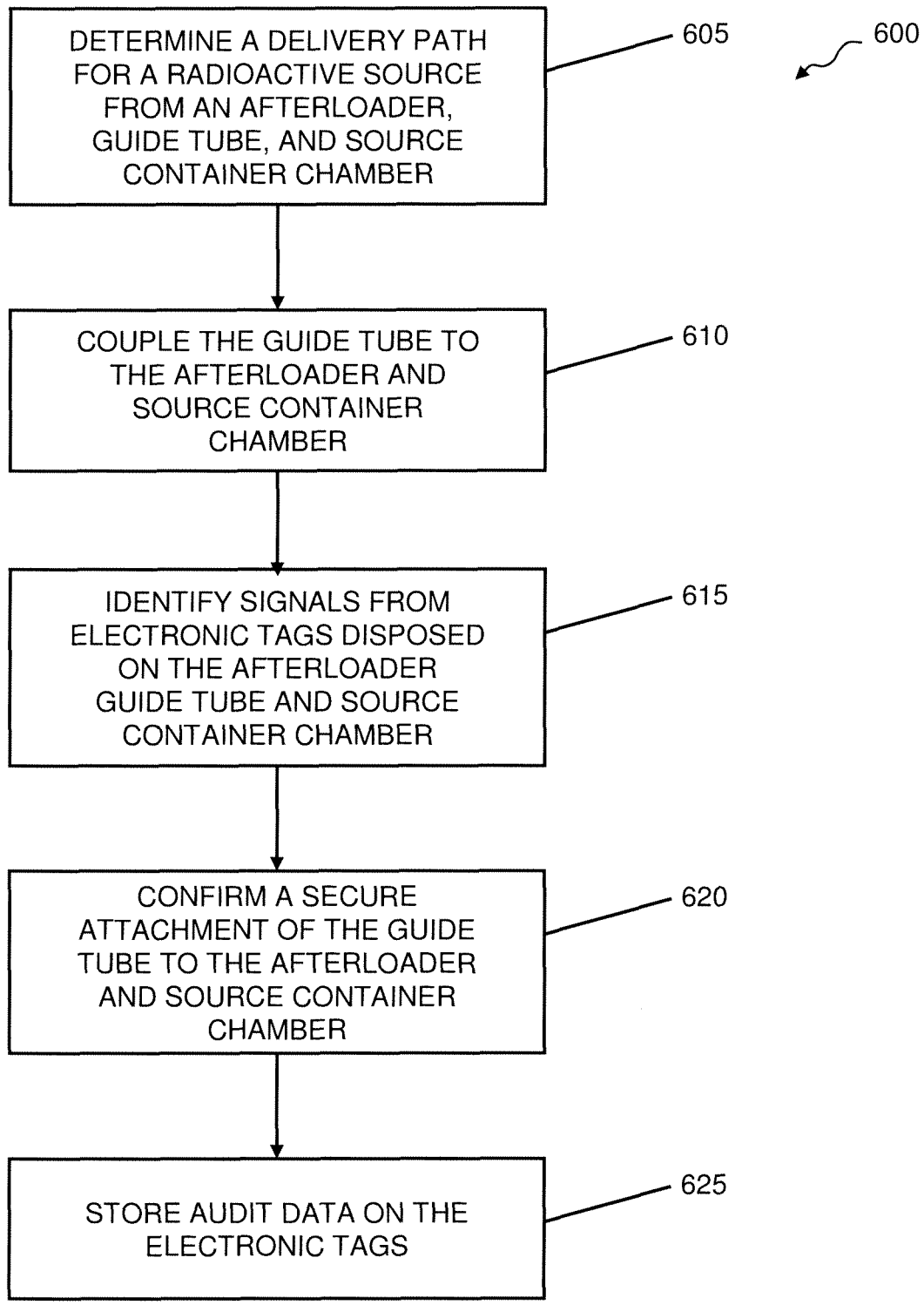
FIG. 10 illustrates a block diagram of another method to track and identify radioactive sources used with an afterloader.

FIG. 10 illustrates a block diagram 600 of another method to track and identify radioactive sources used with an afterloader, and in particular for the uploading or downloading of a radioactive source from a source container chamber (e.g., chamber 310) coupled to the afterloader. For example, in order to download a radioactive source from the afterloader to a source container chamber, the correct path must be selected from the afterloader through the guide tube and into the source container chamber, block 605. In one embodiment, the afterloader may include multiple radioactive sources disposed within individual channels that lead to ports for coupling to guide tubes, as well as multiple guide tubes coupled to the ports. A first end of a guide tube is coupled to the afterloader and a second end of the guide tube is coupled to the source container chamber, block 610. In one example for downloading a radioactive source, a determination may be made to deliver a radioactive source through port #4 of the afterloader, through guide tube #4, and into source container channel #4 of a multi-channel source container chamber.

After the guide tube is coupled to the afterloader and source container chamber, a controller disposed on the afterloader identifies signals from electronic identification tags disposed on the afterloader, guide tube, and source container chamber to confirm that the correct path has been established to send the radioactive source, block 615. For example, if the controller recognizes that guide tube #4 is coupled to port #7 instead of guide tube #4, the controller may indicate to the operator that an incorrect coupling exists. As stated before, in one embodiment, afterloader controller automatically adjusts the program to take into account the error. In one embodiment, the electronic identification tags may be RFID tags (e.g., tags 330, 332). In addition to verifying that the correct delivery path exists, the electronic tags may also confirm that the guide tube is securely attached to the afterloader and source container chamber (e.g., through the interfaces 326, 328 of guide tube 320), block 620. In one embodiment, the signal from the RFID tag disposed on the source container chamber may be relayed through the RFID tag disposed on the guide tube in order to reach the RFID tag disposed on the afterloader. Data may be written and stored on the electronic tags to provide audit information for the device component, block 625. This may include, for example, radioactive source serial number, source activity, and calibration data.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An apparatus, comprising:
a first housing for a radioactive source;
a second housing for the radioactive source; and
a guide tube to couple the first housing with the second housing, wherein the first housing has a first electronic tag, the second housing has a second electronic tag, and the guide tube has a third electronic tag, wherein the first housing, the second housing and the guide tube use at least the three electronic tags to communicate with each other to confirm automatically a delivery path for the radioactive source, wherein communication comprises signaling information related to a first coupling of the first housing to one end of the guide tube and signaling information related to a second coupling of the second housing to a different second end of the guide tube by relaying from the second electronic tag to the first electronic tag through the third electronic tag, the information related to the second coupling of the second housing to the different second end of the guide tube.

2. The apparatus of claim 1, wherein each of the first, second, and third electronic tags comprise a radio frequency identification tag for wireless communication of information between each electronic tag.

3. The apparatus of claim 2, wherein the radio frequency identification tags are disposed on a surface of the first housing, second housing, and guide tube.

4. The apparatus of claim 2, wherein the radio frequency identification tags are embedded within the first housing, second housing, and guide tube.

5. The apparatus of claim 1, wherein the first housing comprises an afterloader and the second housing comprises an applicator to form the delivery path for the radioactive source to a patient.

6. The apparatus of claim 5, wherein the afterloader further comprises a plurality of ports to couple to the guide tube, and wherein the first electronic tag contains information related to a first port that is coupled to the guide tube.

7. The apparatus of claim 6, wherein the applicator further comprises a plurality of channels to receive the radioactive source, and wherein the second electronic tag contains information related to a first channel that is coupled to the guide tube.

8. The apparatus of claim 1, further comprising a controller to determine that a coupling of the guide tube and the first and second housing is incorrect for a prescribed plan to use the delivery path for the radioactive source and to adjust the prescribed plan.

9. The apparatus of claim 1, wherein communicating further comprises identifying the delivery path as an incorrect path in a prescribed plan;
selecting the delivery path for the prescribed plan after identifying the delivery path as being incorrect for the prescribed plan; and
adjusting the prescribed plan to incorporate the selected delivery path as a correct delivery path for the prescribed plan.

10. The apparatus of claim 1, wherein signaling information comprises communicating at least two of an applicator identification number, an applicator manufacture date, an applicator usage cycle, and an applicator sterilization period.

11. The apparatus of claim 1, wherein signaling information comprises wireless communication.

12. The apparatus of claim 1, further comprising one of a radioactive wire to extend through the delivery path, and a radioactive capsule to be delivered through the delivery path.

13. The apparatus of claim 1, wherein communication comprises:

directly signaling from the third electronic tag to the first electronic tag, information related to a first coupling of the first housing to one end of the guide tube;

directly signaling from the second electronic tag to the third electronic tag information related to a second coupling of the second housing to a different second end of the guide tube; and relaying to the first electronic tag through the third electronic tag, the information related to a second coupling of the second housing to a different second end of the guide tube.

14. An apparatus, comprising:

a first radio frequency identification device tag disposed on a radioactive source afterloader;

a second radio frequency identification device tag disposed on a radioactive source applicator;

a third radio frequency identification device tag disposed on a guide tube to couple the radioactive source afterloader with the radioactive source applicator; and a radio frequency identification device tag controller disposed on the radioactive source afterloader to coordinate communication between the first, second, and third radio frequency identification device tags, wherein coordinating comprises identifying signals from the first, second, and third radio frequency identification device tags, and wherein coordinating comprises relaying signals from the second radio frequency identification device tag to the first radio frequency identification device tag through the third radio frequency identification device tag.

15. The apparatus of claim 14, wherein the radio frequency identification device tag controller receives signals from the first, second, and third radio frequency identification device tags related to the coupling of the guide tube with the radioactive source afterloader and the radioactive source applicator.

16. The apparatus of claim 15 wherein the radio frequency identification device tag controller receives signals from the first, second, and third radio frequency identification device tags related to audit information.

17. The apparatus of claim 15, wherein the radioactive source afterloader comprises a plurality of ports to couple with the guide tube, and wherein the radio frequency identification device tag controller receives information from the first radio frequency identification device tag related to a first port coupled to the guide tube.

18. The apparatus of claim 15, wherein the radioactive source applicator comprises a plurality of channels to couple with the guide tube, and wherein the radio frequency identification device tag controller receives information from the second radio frequency identification device tag related to a first channel coupled to the guide tube.

19. The apparatus of claim 14, wherein the afterloader further comprises one of a radioactive wire to extend through the guide tube and to the applicator, and a radioactive capsule to be delivered through the guide tube and to the applicator.

20. An apparatus, comprising:

a radiation source delivery path having electronic tags disposed on each of a first guide tube, a multi-channel afterloader, and a multi-channel applicator, the electronic tags are configured to signal information to identify attachment of a first end of the first guide tube to a first port of the multi-channel afterloader and a second opposite end of the first guide tube to a first channel of the multi-channel applicator, wherein signaling information comprises relaying to the multi-channel afterloader through the electronic tag disposed on the first guide tube, the information to identify attachment of second opposite end of the first guide tube to a first channel of the multi-channel applicator.

21. The apparatus of claim 20, wherein each electronic tag comprises a radio frequency identification tag for wireless communication of information between the electronic tags.

22. The apparatus of claim 21, wherein the multi-channel afterloader comprises a radio frequency identification device tag controller to coordinate the communication between the radio frequency identification device tags in response to receiving signals from the tags related to the coupling of the first guide tube with the radioactive source afterloader and the radioactive source applicator.

23. The apparatus of claim 20, further comprising a plurality of guide tubes in addition to the first guide tube; wherein the afterloader further comprises a plurality of radioactive wires to extend through the guide tubes to the applicator, or a plurality of radioactive capsules to be delivered through the guide tubes to the applicator.

* * * * *